(12) United States Patent
Burr et al.

(10) Patent No.: US 6,440,118 B2
(45) Date of Patent: *Aug. 27, 2002

(54) DEVICE AND METHOD TO SENSE BODY SUBSTANCE TRANSITION

(76) Inventors: Lawrence S. Burr, 21 Walsh La., Fairfax, CA (US) 94930; Kenneth N. Matsumura, 2107 Dwight Way, Berkeley, CA (US) 94704

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/309,690

(22) Filed: May 11, 1999

(51) Int. Cl.$^7$ .......................... A61M 5/00; A61M 31/00

(52) U.S. Cl. ...................... 604/503; 604/272; 604/239; 604/116; 607/116

(58) Field of Search ................. 604/93.01, 264, 604/272, 116–117, 503, 506–508; 600/372, 373, 381, 393, 547, 504–506; 607/2, 3, 116

(56) References Cited

U.S. PATENT DOCUMENTS

| | | | | |
|---|---|---|---|---|
| 3,682,162 A | * | 8/1972 | Colyer | 600/373 |
| 4,690,152 A | | 9/1987 | Juncosa | |
| 5,078,714 A | * | 1/1992 | Katims | |
| 5,080,104 A | | 1/1992 | Marks | |
| 5,271,413 A | * | 12/1993 | Dalamages et al. | |
| 5,294,325 A | * | 3/1994 | Liu | 204/416 |
| 5,306,236 A | * | 4/1994 | Blumenfeld et al. | 604/21 |
| 5,423,877 A | * | 6/1995 | Mackey | 128/698 |
| 5,429,636 A | * | 7/1995 | Shikhman et al. | 606/41 |
| 5,515,848 A | * | 5/1996 | Corbett et al. | 600/377 |
| 5,972,416 A | * | 10/1999 | Reimels et al. | 427/2.12 |
| 6,112,123 A | * | 8/2000 | Kelleher et al. | 606/27 |
| 6,148,666 A | * | 11/2000 | Roesicke | 340/620 |
| 6,241,710 B1 | * | 6/2001 | VanTassel et al. | 604/264 |
| 6,244,214 B1 | * | 6/2001 | Hebrank | 119/6.8 |

* cited by examiner

Primary Examiner—Brian L. Casler
Assistant Examiner—Catherine Serke
(74) Attorney, Agent, or Firm—David Fink; Timothy W. Johnson

(57) ABSTRACT

In a hypodermic needle having an end that attaches to a syringe, an elongated hollow shaft for passing fluid terminated at a sharpened point; the improvement comprising an electrically insulating layer positioned on the shaft and at least one electrically conductive area positioned on the insulating layer. The electrically conductive area being adapted to be connected to an electrical source.

A method of determining when a hypodermic needle penetrates into tissue, vein, or lumen by providing an electrical source; connecting the electrical source electrically to a hypodermic needle designed to provide two electrically conducting portions, spaced apart from each other, and near a point on the hypodermic needle. Providing an electrical current sensing mechanism in an operating relationship to the electrical current provided by the electrical source, whereby the electrical current sensing mechanism detects the variation in the electrical current between the conducting portions to enable the identification of the change of the electrical current between an electrically conductive environment and a different electrically conductive environment.

A system for determining when a hypodermic needle penetrates into tissue, vein, or lumen. The system comprises a hypodermic needle having two electrically conducting portions, spaced apart from each other, and near a point on the hypodermic needle, and electrically insulated from each other. The conducting portions being adapted to be connected to an electrical source to enable electrical current to flow through the conducting portions. The system has an electrical source electrically connected to the conducting portions. The system has a mechanism for determining the change in the electrical current between the conducting portions when the hypodermic needle is penetrating a body and a signaling device for generating a signal indicating when the conducting portions have penetrated the body and reached a predetermined position.

4 Claims, 13 Drawing Sheets

AUDIBLE OSCILLATOR

COMPREHENSIVE PARTS LIST

INPUT STAGE
RINF 1.8 MEG 1%
CINF .022 µF POLCARB
TINB 10 E 20-TURN
CINB 1 µF

ABSOLUTE VOLTAGE F.W. RECTIFIER
RAB1 499K 1% FILM
RAB2 499K 1% FILM
DAB1 1M914 DIODE
DAB2 1M914 DIODE
RAB3 2E 5% FILM
CAB1 .1 µF TANTALUM

PANEL CONTROLS
VOLUME 10K LINEAR
SENSITIVITY 10K LINEAR
BALANCE (OBSOLETED)
CENTER FREQ. 100K LOG.

NOTE LINEAR POT VALUES
CAN BE 10K TO 100K.
LOG POT VALUE CAN ALSO
BE 10K TO 100K

OFFSET ADJUST
ROSI 499K 1% FILM
ROSF 499K 1% FILM
TOSI 10K 20-TURN
COSB .33 µF CERAMIC

18dB/OCT. LOWPASS
RLP1 150K 5%
CLP1 .022 µF FILM
RLP2 240K 5%
CLP2 .022 µF FILM
RLP3 240K 5%
CLP3 .1 µF FILM

VARIOUS NOTES ABOUT COMPONENT SELECTIONS
UNSPECIFIED TRIM POT VALUE CAN BE ANY FROM 10K TO 1 MEG

HEX INVERTER EQUIVALENTS ARE OK, INCLUDING 2 OR 3 INPUT NAND GATES
WITH INPUTS TIED TOGETHER. ALL GATES <u>UNBUFFERED</u> TYPES.

PANEL CONNECTOR DESIGNATIONS
RED +V SUPPLY
     FOR EXTERNAL MODULES
YLO DATAQ CHANNEL #2
GRN GROUND
BLK DATAQ CHANNEL #1,
    PROBE INPUT

— RESISTOR
— CAPACITOR
— TEST PIONT
— ZERO VOLTS COMMON GROUND
— ALUMINUM ELECTROLYTE UNLESS OTHER IS SPECIFIED
— OPERATIONAL AMPLIFIER
— HOST INVERTER CMOS OB TYPE

*FIG. 4A*

DEVICE AND METHOD TO SENSE BODY SUBSTANCE TRANSITION

BACKGROUND OF THE INVENTION

In the prior art there exists a deficiency in the methods and devices used in the introduction of a hypodermic needle into venous or arterial blood vessels of humans and animals. Often times the person administering the syringe needle will penetrate through the blood vessel or miss the blood vessel altogether. Such mishaps can cause severe agitation and pain to patients. The problem even persists among trained phlebotomists. The problem occurs more often where the blood vessels are difficult to see or palpate under tissues. In such areas discerning the depth and position of the blood vessel becomes even more difficult. Additionally, positioning of the blood vessel may be misjudged because blood vessels tend to move as the needle advances. Indeed, even experienced phlebotomists often miss the vessel or just stab through it.

Devices in the prior art have been used to enhance needles to provide needle tip position relative to a blood vessel. One such device is the "Smart Needle". The "Smart Needle" utilizes an ultrasonic doppler probe placed within the tubular needle bore such that some reflectance cuing of the needle tip position relative to a blood vessel wall is provided to the operator. A drawback of the "Smart Needle" is that lumen definition is not provided. Due to its size the Smart Needle is limited to the relatively large diameter of needle gauges 18 to 22. The present invention is able to attain a gauge size 30 which is sufficiently narrow to treat pediatric or veterinary subjects. Additionally, the indicating means unit of the Smart Needle is relatively large and must be connected to the penetrating means via a five foot long coaxial cable. The one-time use only needles costs $70.00 per needle unit in packs often each.

Other devices in the prior art distinguish between adipose and muscle tissues or vascular transition. One such device is described in U.S. Pat. No. 5,271,413 entitled Method to Sense the Tissue for Injection from a Hypodermic Needle. The device described in the aforementioned patent utilizes bioimpedance to define the transition between adipose and muscle tissues or vascular transition. These devices aid in the introduction of drug agents into specific tissues enabling proper tissue absorption. These devices do not address blood vessel structures and are not capable of discriminating, proximity locating, or lumen defining. The device and method described in the '413 Patent uses an electrode positioned on the skin surface and the needle to introduce a signal into the body and detect the impedance with the reference electrode. These measurements are then used to determine the type of tissue in which the needle is currently located. Accurate results require the reference electrode to be placed some distance from the needle target area and the needle to penetrate into the tissue 2 to 5 millimeters.

BRIEF SUMMARY OF THE INVENTION

One embodiment according to the invention is a hypodermic needle having an end that attaches to a syringe and an elongated hollow shaft for passing fluid terminated at a sharpened point; the improvement comprising an electrically insulating layer positioned on the shaft and at least one electrically conductive area positioned on said insulating layer; said electrically conductive area being adapted to be connected to an electrical source.

A method according to the invention is a method of determining when a hypodermic needle penetrates into tissue, vein, or lumen. The method comprises providing a hypodermic needle having two electrically conducting portions, spaced apart from each other, and near a point on the hypodermic needle, and electrically insulated from each other. The conducting portions being adapted to be connected to an electrical source to enable electrical current to flow through said conducting portions. Next, determining the change in the electrical current between the conducting portions when the hypodermic needle is penetrating a conductive body. Finally, generating a visual and/or audible signal indicating when the conducting portions have penetrated the conductive body and reached a predetermined position.

Yet another embodiment of the invention is a system for determining when a hypodermic needle penetrates into tissue, vein, or lumen. The system comprising a hypodermic needle having two electrically conducting portions, spaced apart from each other, and near a point on the hypodermic needle, and electrically insulated from each other. The conducting portions being adapted to be connected to an electrical source to enable electrical current to flow through them. An electrical source electrically connected to the conducting portions. A means for determining the change in the electrical current between said conducting portions when the hypodermic needle is penetrating a body and a signaling means for generating a visual and/or audible signal indicating when the conducting portions have penetrated the body and reached a predetermined position.

DETAILED DESCRIPTION OF THE INVENTION

The invention takes advantage of the differing conductive properties of body tissues, veins, and lumen. The conductivity of a body substance is measured using electrodes positioned on the needle shaft. An electric current is introduced into the body substance and the conductivity is measured. The change in conductivity signifies a transition of the needle from one body substance to another. For example a needle passing through a body tissue will have a lower conductivity than when the needle penetrates into a vein which has an aqueous conductive volume, at which point the amount of current flow increases. Taking advantage of these electrical properties allows for the efficient determination of when a penetrating hypodermic needle has reached a predetermined point.

Figure 1A:
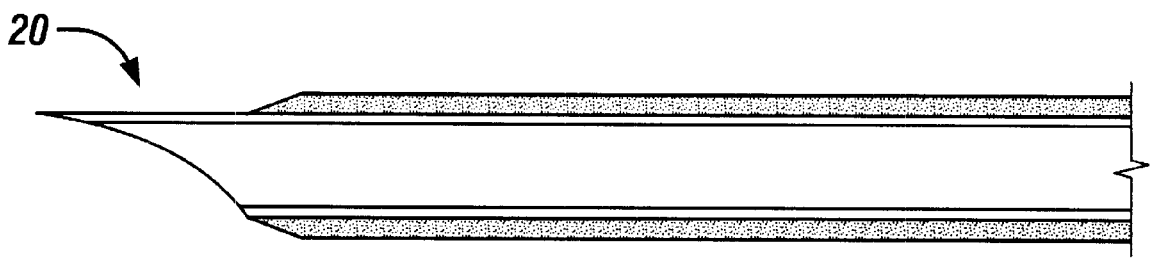
FIGS. 1a, 1b and 1c are cross sectional views of prior art electrode needles on an enlarged scale.
Figure 1B:
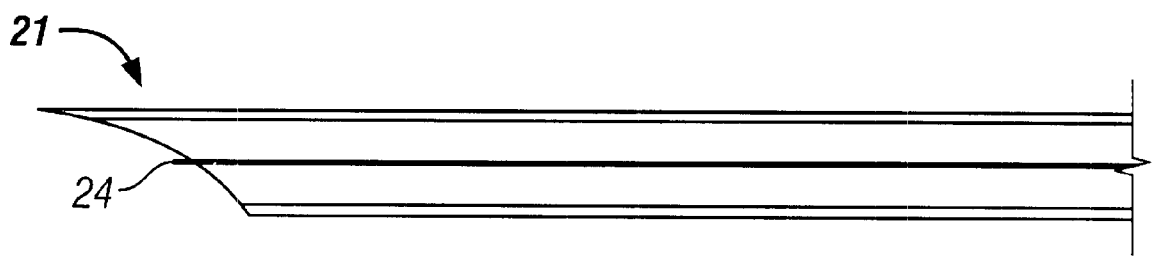
Figure 1C:
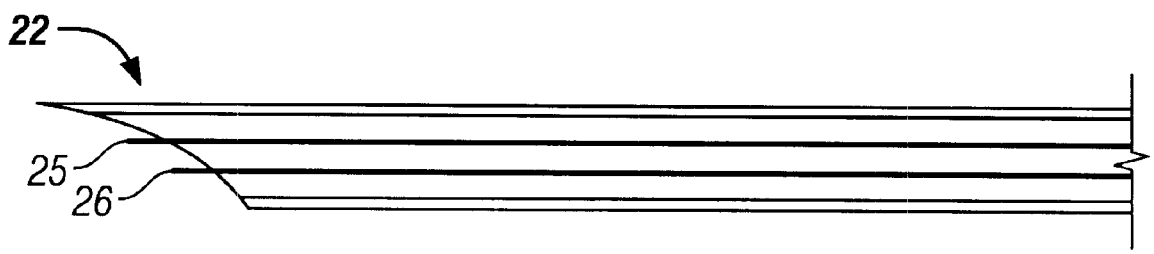

FIGS. 1a, 1b, and 1c show prior art electrode needles. These needles were used to locally anaesthetize patients and also to passively sense bioelectric energy. Needle 20 in FIG. 1a is an insulated hypodermic needle, or surgical needle. It is often referred to as a "nerve block" needle electrode, in a case where a pain killer may be injected to numb an electro-shock or sensing in very pain sensitive areas of the body. Needle 20 has no electrode. Needle 21 in FIG. 1b is a single ended concentric needle electrode or a hypodermic needle with one thinly insulated platinum wire electrode 24 threaded through it. Needle 22 in FIG. 1c is a differential concentric needle electrode. It is a hypodermic needle with two thinly insulated platinum conductors 25 and 26. Needle 21 and 22 were used for the passive sensing of bio-electric activity manufacture of these needles was expensive due to the high cost of platinum.

Figure 2:
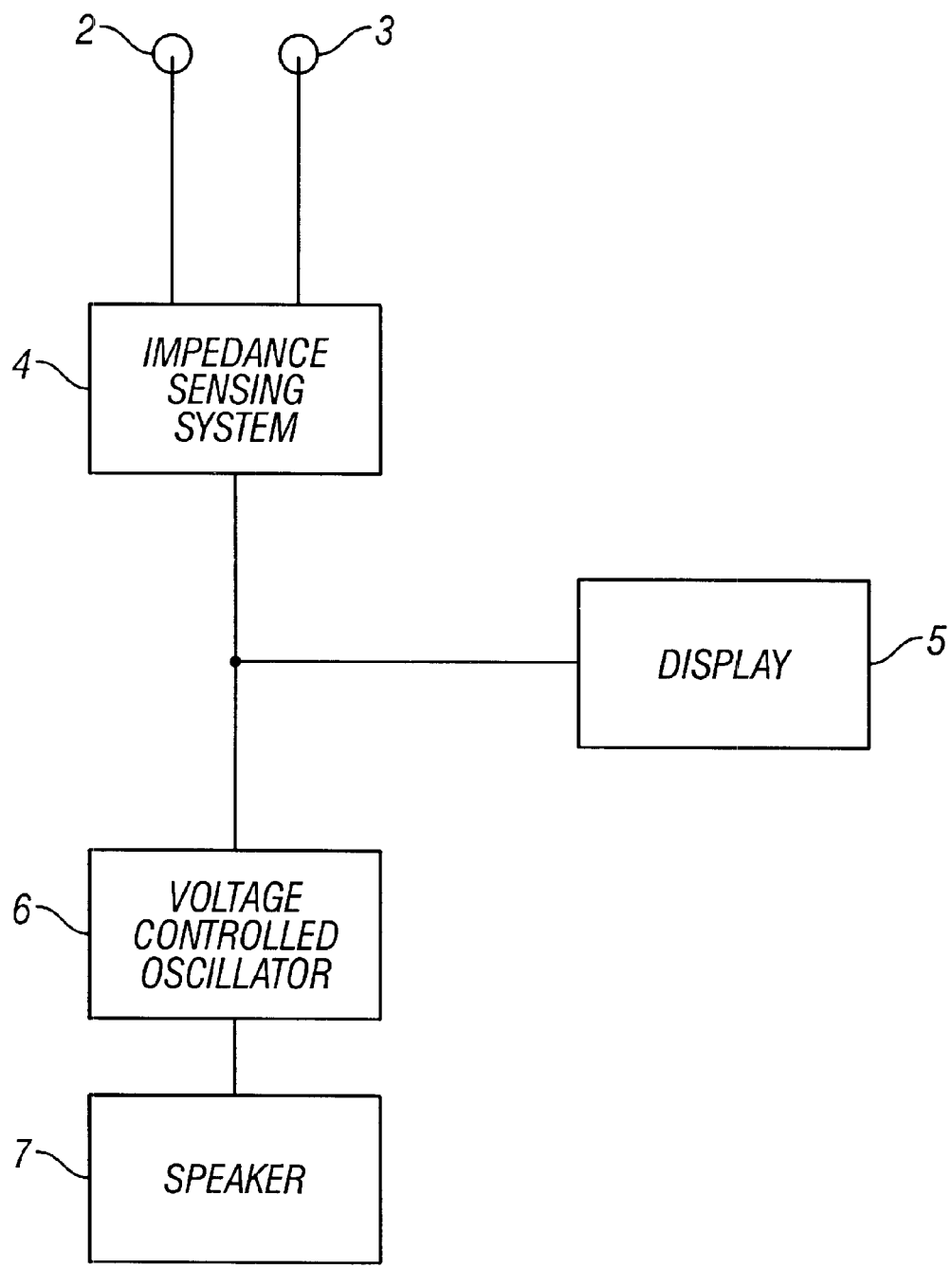
FIG. 2 is a block diagram of an embodiment according to the invention.
Figure 3A:
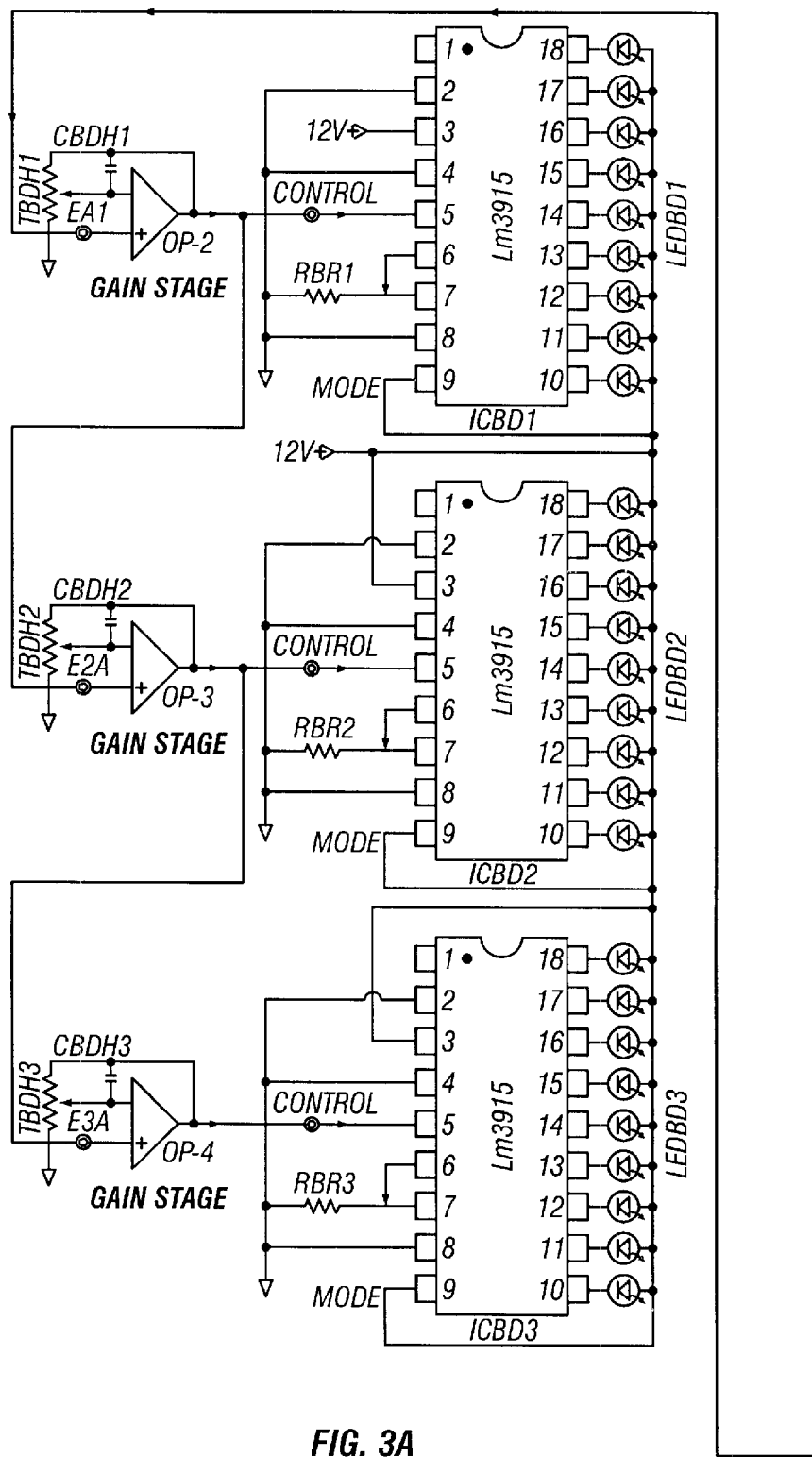
FIG. 3 shows an electrical schematic of a system that accepts the input from electrodes and detects differences in conductance.
Figure 3B:
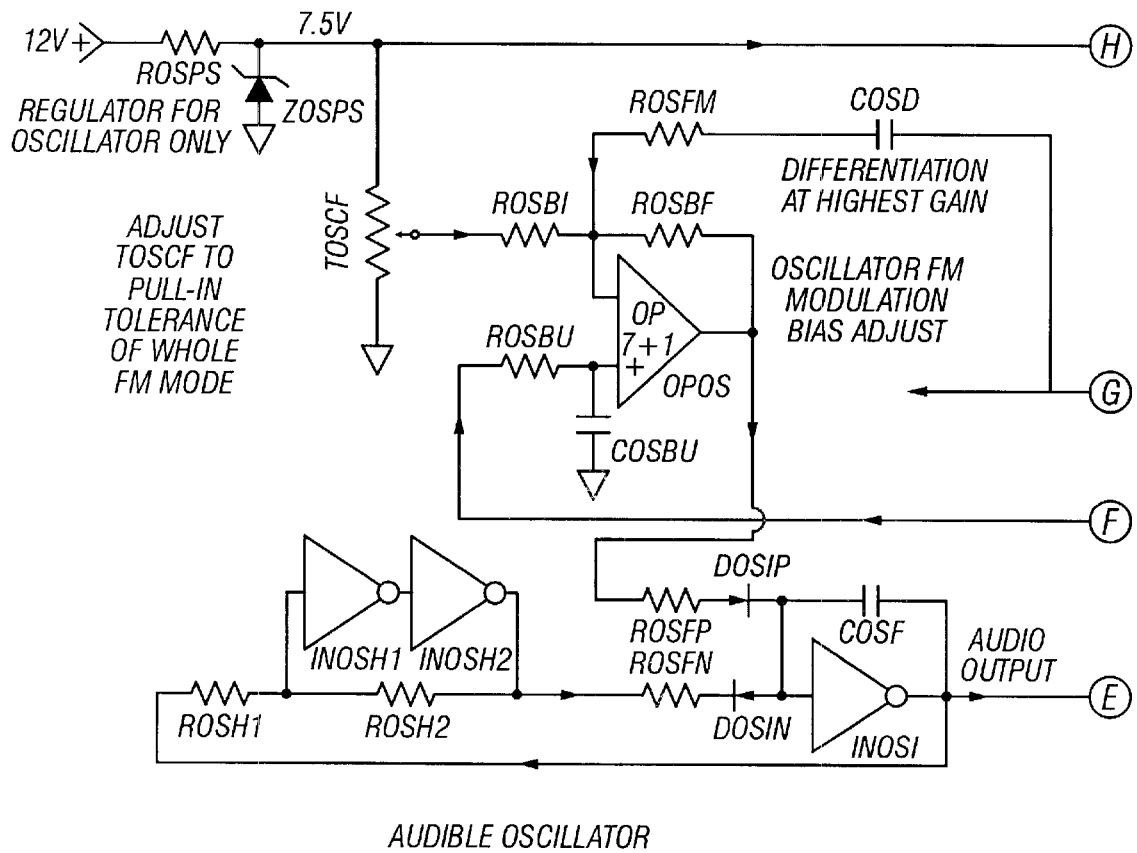
Figure 3B:
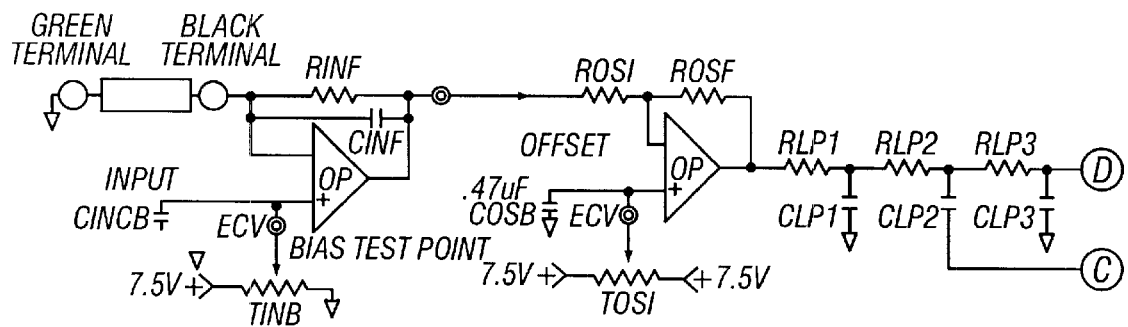
Figure 3C:
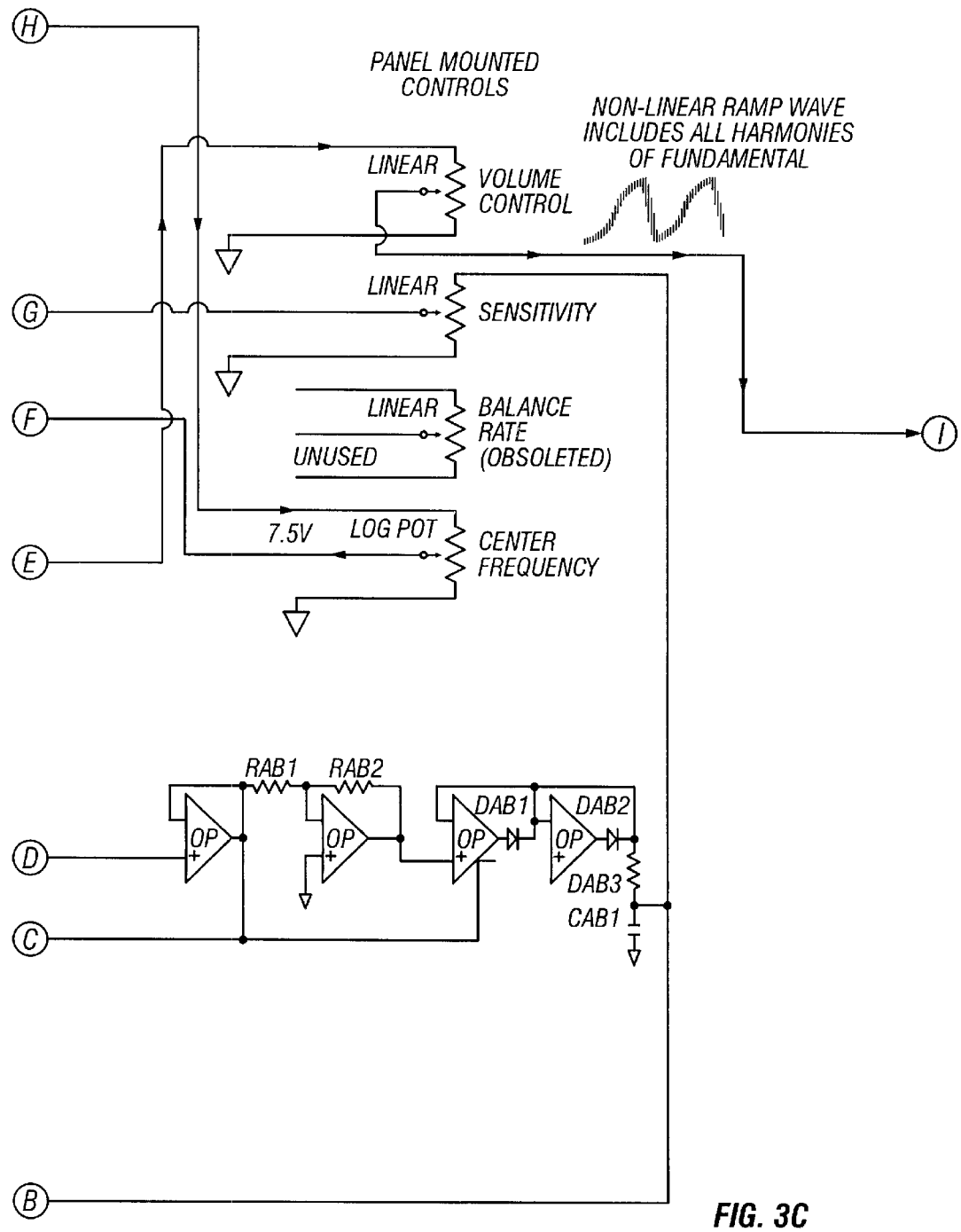
Figure 3D:
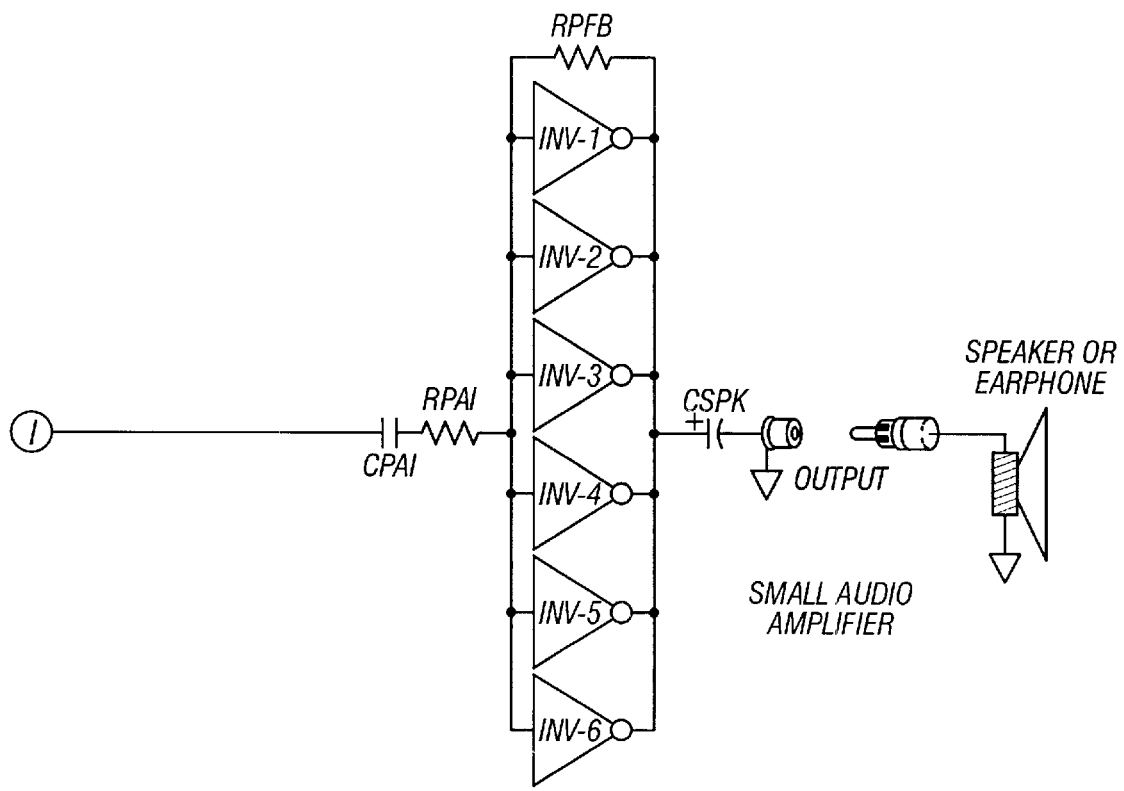

FIG. 2 shows a block diagram of the flow of signals in one embodiment according to the invention. Electrodes 2 and 3, which represent electrodes located on the tip of a needle (not shown) or one electrode could be the needle shaft itself and the other electrode be located on and insulated from the tip of the, are introduced to biological tissues as a needle is inserted into living tissue. The signals from electrodes 2 and 3 are received by the impedance sensing system 4. Sensing system 4 is a prior art design to measure current as a change is introduced into a system. One of the inputs is referenced to ground, or a defined "common" point. The system 4 injects 0.1 volt across the tissues contacted by electrodes 2 and 3 and then detects the micro-currents. The system 4 processes the micro-currents with noise reduction, low-pass filtering, and full wave rectification. The detected micro-currents are thereby converted to voltages, which are amplified, displayed and fed to the control of a voltage controlled oscillator 6. The oscillator 6 is a voltage controlled oscillator ("VCO"); changes in the control voltage of the VCO produce changes in the frequency of the VCO. To provide the effect of an auto-zeroing or self-balancing, the control voltage is AC coupled to differentiate the wide ranging input signal. As a result of this control voltage processing, the sound generated by the speaker 7 will drift to whatever center frequency the operator deems to be most pleasing. The amplified voltage from the sensing system 4 is also fed to display 5 where information concerning the voltage is indicated.

It is common in instrumentation design to use three inputs, one ground, second being an inverting input. This differential design is used primarily to cancel "common mode" signals such as 60 Hz noise which is omnipresent and a large source of interference for fast measurement. To aid in avoiding interference and making the noise filtering easier, a refresh rate of 20 Hz was chosen.

Figure 4B:
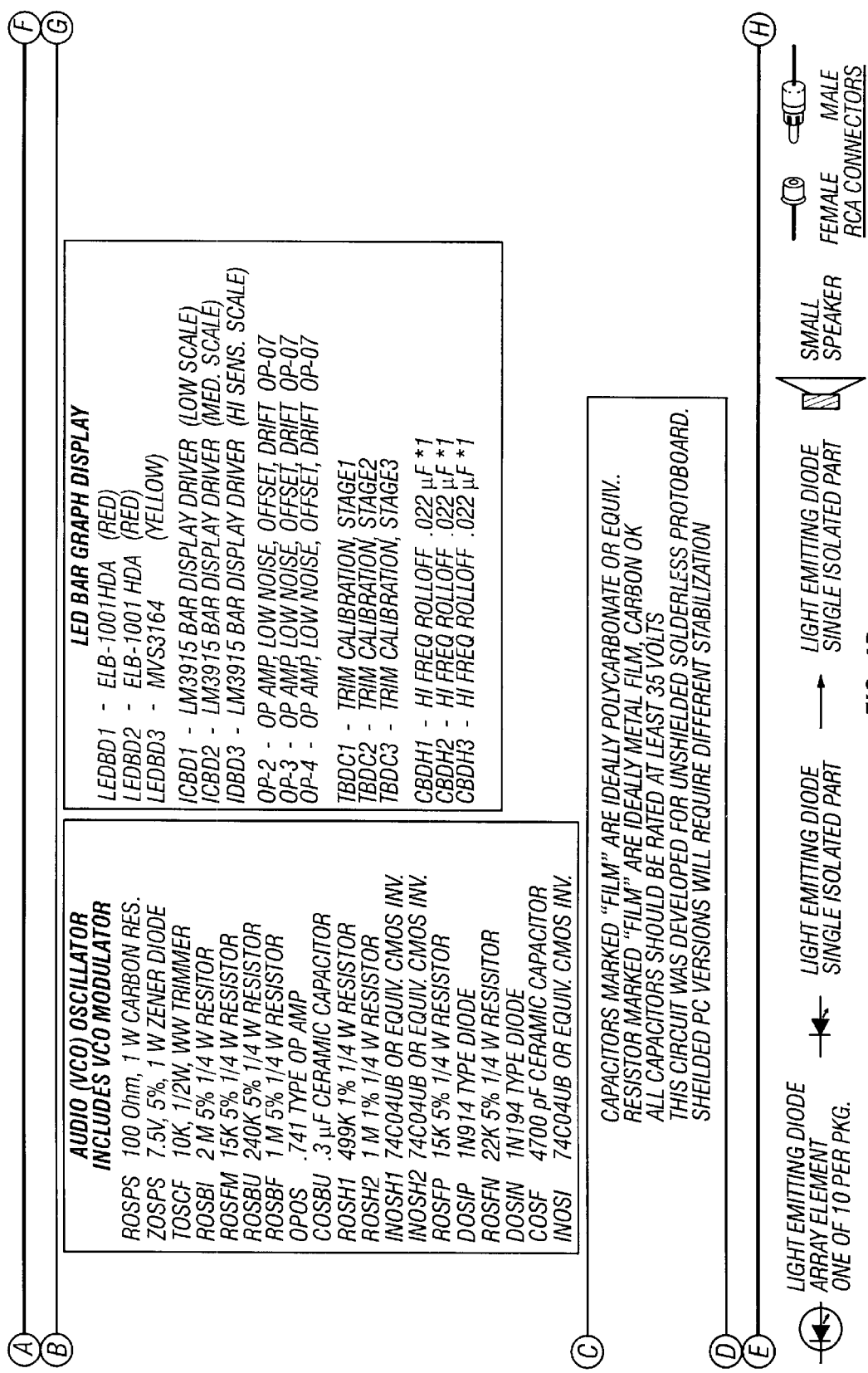
FIG. 4 shows a comprehensive parts list and legend for the schematic in FIG. 3.
Figure 4C:
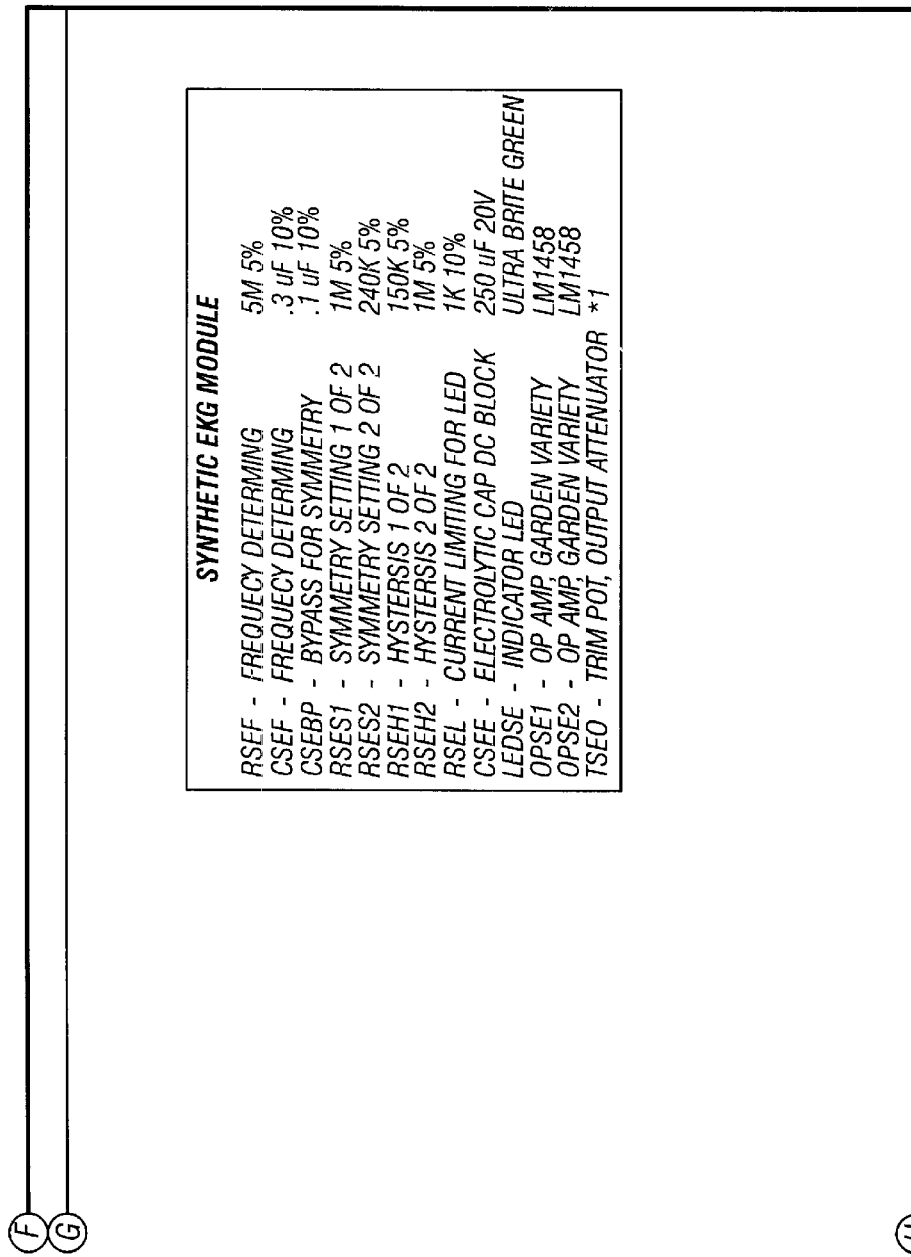
Figure 4C:
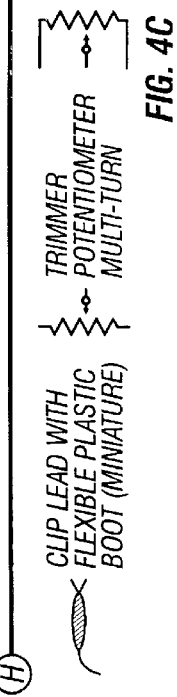

The components and circuitry used in the invention to detect changes in micro-currents are well known in the prior art and well within the skill of the prior art. The equipment can be assembled from commercially available parts. FIG. 3 shows one embodiment of the invention. FIG. 3 shows electrical schematic to be connected. FIG. 3 should be viewed in concert with FIG. 4 which shows a comprehensive parts list for the schematic shown in FIG. 3.

Figure 5A:
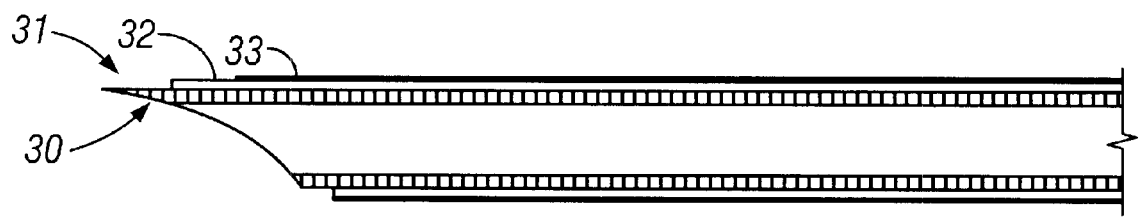
FIGS. 5a and 5b are cross sectional views of a trilaminate needle electrode according to the invention taken through and perpendicular to the axis of the needle respectively.
Figure 5B:
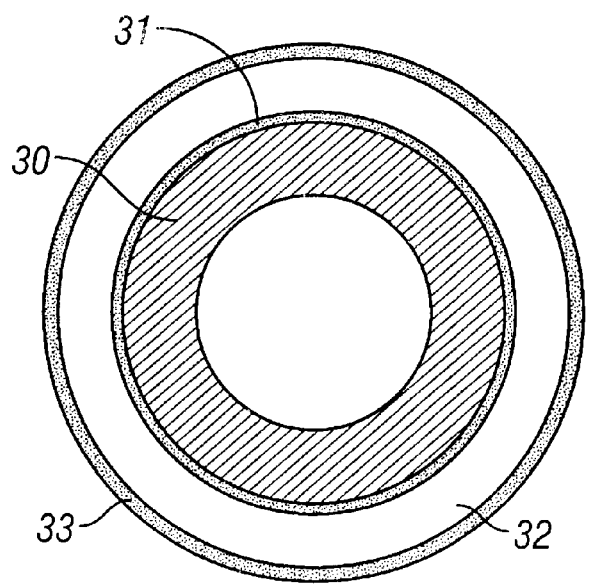

Trilamination is used to layer or laminate certain materials over the surface of a hypodermic needle. A layer may be an insulator layer made of dielectric enamel or polymer or some other insulating material. The layer may be a conductive layer made from a conductive substance like suspended conductive silver enamel, vacuum deposited metallic layer, or conductive polymer. Polytetrafluoroethylene, sold under the trademark TEFLON, may be used for the outer layer providing for easy low-friction insertion into the tissue, other non-electro-conductive materials may also be used. FIGS. 5a and 5b show two cross sections of a trilaminated needle electrode of fully coaxial design where each layer completely encircles the needle. The sequence of layers starting at the needle steel 30 outward is the inner insulator 31, which is made of dielectric enamel, conductive layer 32, which is suspended silver enamel or a vacuum deposited metallic layer, and outer layer 33, which is the same dielectric enamel as inner insulator 31 or could be TEFLON.

Figure 6:
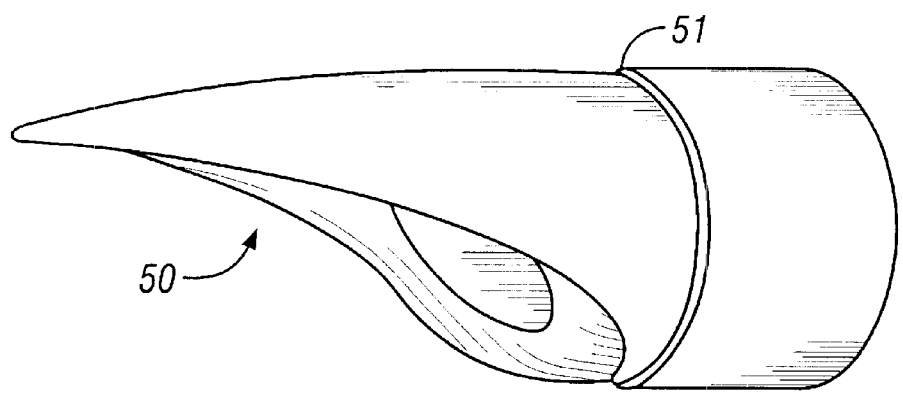
FIG. 6 is a perspective view of the penetrating end of a trilaminate needle electrode according to the invention on an enlarged scale with portions removed to show hidden portions.
Figure 7:
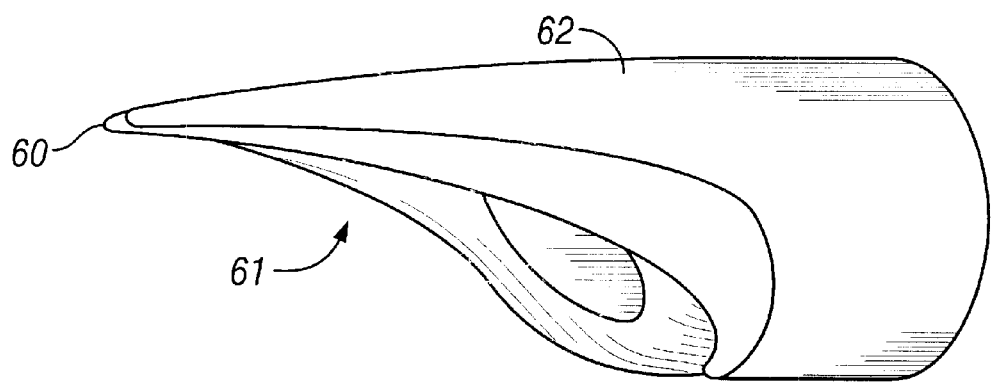
FIG. 7 is another perspective view of the penetrating end of a trilaminate needle electrode according to the invention on an enlarged scale with portions removed to show hidden portions.
Figure 8:
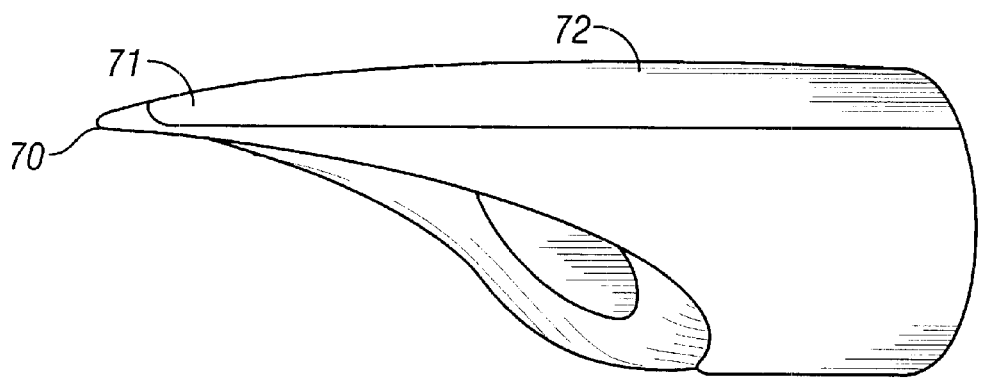
FIG. 8 is another perspective view of the penetrating end of a trilaminate needle according to the invention on an enlarged scale with portions removed to show hidden portions.

In the ideal Trilaminate Needle Electrode, the electrical sensitivity is confined to the extreme tip only, as shown in FIGS. 7 and 8, not the 360° ring-shaped conductive sensitive layer 51 encircling the needle 50 in FIG. 6. Confining the electrode or electrodes to the extreme tip increases the response time for determining a change in electrical current and a change from one electrically conductive environment to another electrically conductive environment, such as penetrating a vein. The trilaminate needle electrode in FIG. 6, requires that the entire piercing end of the hypodermic needle 50 must penetrate the tissue or vein before the conductive sensitive layer 51 encounters the tissue or vein and a change in conductance is measured.

To create a Trilaminate Needle Electrode of fully coaxial design as in FIGS. 5a and 5b, a standard intravenous needle core 30 is coated first in insulating enamel or other dielectric material, then in conductive enamel 32, or other conductive material, then again in an insulating layer 33 such as TEFLON. FIG. 6 also shows these respective layers. The sensitive conductive area 51 which is exposed near the tip is 360° ring-shaped since the sensitive conductive layer 51 completely encircles the needle as shown in FIG. 6. A 360° contact area is less likely than a point to have the sensor resolution to detect a vein wall-to-lumen transition.

Another embodiment according to the invention is shown in FIG. 7. The trilamination is shaped to bring the sensitive area to the foremost point of the needle. The conductive material was extended to the tip of the needle 61. The contact area 60 is smaller, improving the sensor's spacial resolution and being located on the very tip of the needle provides for the earliest warning when penetrating tissue layers. It is essential that the insulation of the outermost layer 62 prevent the sensor area from including any of the edge coated area except for the very tip 60. Fine photolithographic deposition or equivalent are of course needed to print on a cylinder as small as a hypodermic needle.

FIG. 8 shows another embodiment according to the invention. This trilaminate needle electrode eliminates unnecessary lamination. Instead of encircling the needle with lamination for an insulating layer and a conductive layer, a conductive stripe 71 from the needle tip 70 up the needle shaft 72 is laminated onto an insulating layer located on the surface of the needle. Positioning more than one stripe, as in FIGS. 10 and 11a, requires the stripes to be electrically separated. Three stripes could be used with dual differential input for directional sensing in three dimensions. One major advantage of using a stripe instead of 360° wrap of inner insulator and conductive layer, is a decrease in the total diameter of the trilaminate needle electrode as well as conserving the expensive conductive coating material.

Figure 9:
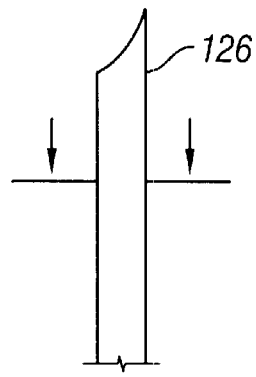
FIG. 9 is a hypodermic needle with a portion removed.
Figure 10:
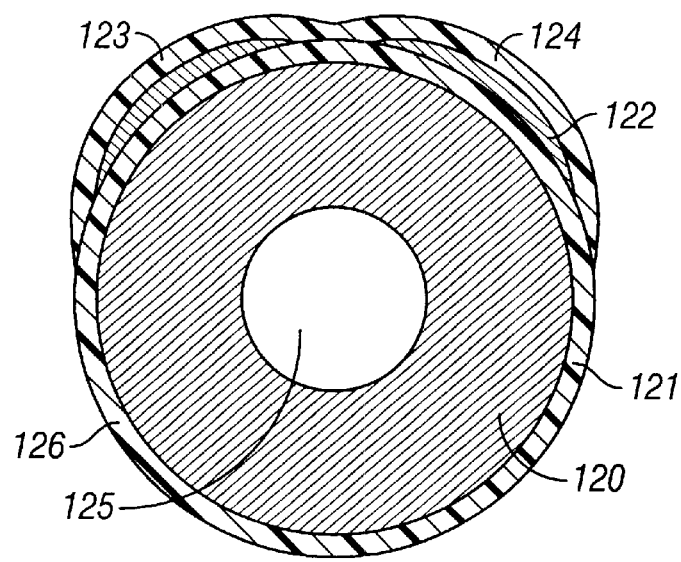
FIG. 10 shows a cross section of the hypodermic needle according to the invention shown in FIG. 9 along line 9, on an enlarged scale.

FIGS. 9 and 10 show a hypodermic needle according to the invention with two electrically conductive areas 123 and 124 that are electrically separated from each other. Insulating layer 121 covers the steel shaft 120 of the hypodermic needle 126. Positioned on insulating layer 121 is conductive area 122 at approximately 30 degrees in width. Also positioned on insulating layer 121 and electrically spaced from conductive area 122 is conductive area 123. Insulating layer 124 covers conductive areas 122 and 123 without encircling the needle shaft. On the hypodermic needle 126, the electrically conductive areas 122 and 123 are used as electrodes, in an electrical circuit, to detect tissues, blood vessels, and vessel lumen.

Figure 11A:
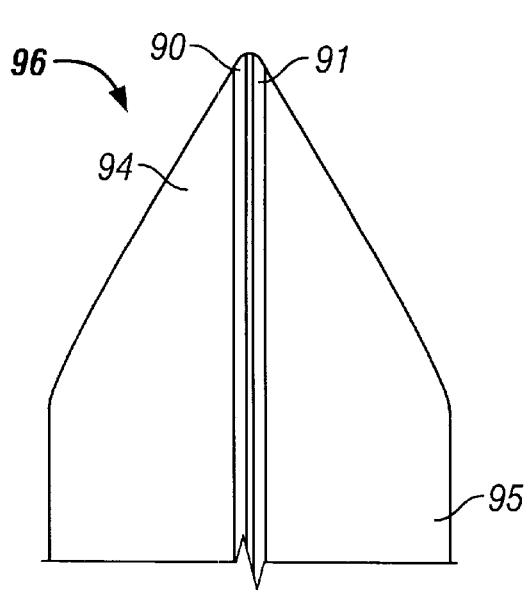
FIG. 11a is a front view of a trilaminate needle electrode according to invention on an enlarged scale with portions removed showing two exposed conductive stripes from the tip of the syringe needle down the needle shaft.
Figure 11B:
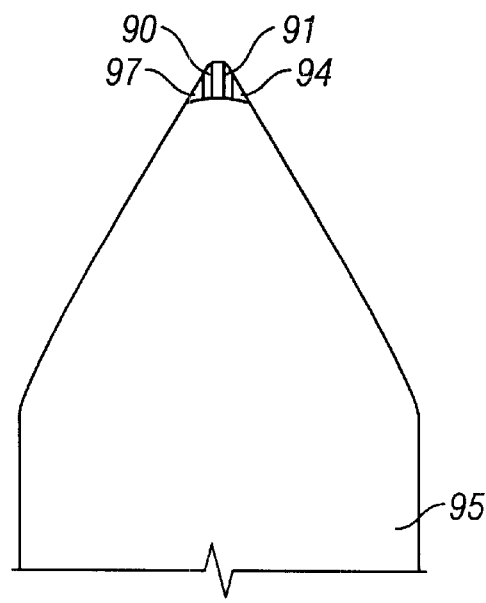
FIG. 11b is a front view of the trilaminate needle in FIG. 11a with an insulating coating leaving only the tips of the conductive stripes exposed.

FIG. 11a shows a trilaminate needle electrode 96 in accordance with the invention on an enlarged scale with portions removed showing two exposed conducting stripes 90 and 91 from the tip of the syringe needle down the needle shaft 95 positioned on insulating layer 94, so that conducting stripes 90 and 91 do not contact the needle shaft 95. FIG. 11b shows an insulating layer 97, like TEFLON, placed over the conducting stripes 90 and 91 and insulating layer 94, leaving only a predetermined amount of each conducting stripe 90 and 91 exposed at the penetrating tip of needle 96. Reducing the amount of conducting stripe 90 and 91 that is exposed increases the sensor resolution by localizing the conductance measuring area. A high sensor resolution allows the system to detect subtle changes in conductance as the needle passes through different tissues or membranes.

Figure 12A:
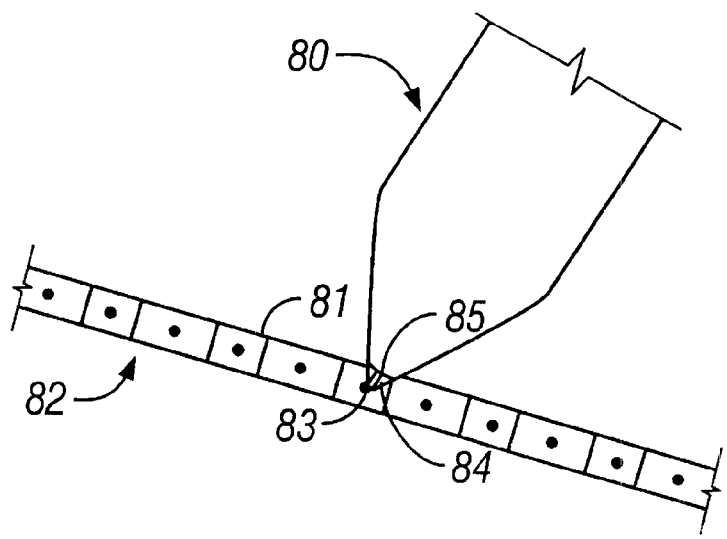
FIG. 12a is a sectional view of a trilaminate needle electrode according to the invention on an enlarged scale penetrating the wall of a vein.
Figure 12B:
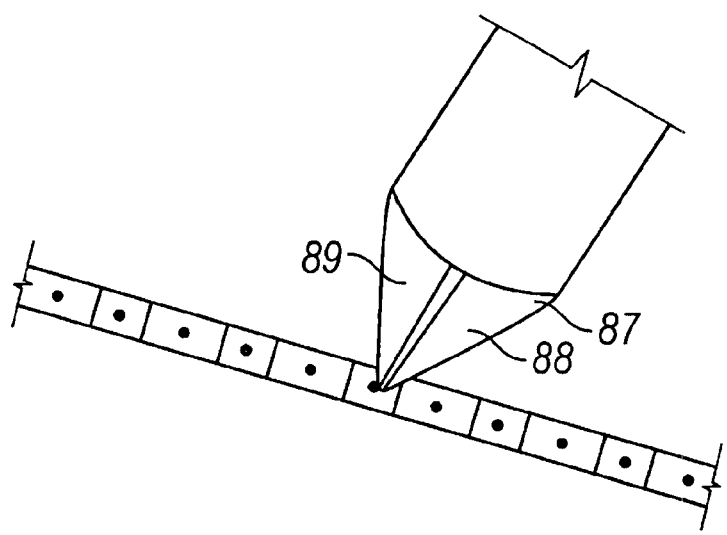
FIG. 12b is a view similar to FIG. 12a with the insulating layer further away from the penetrating tip of the needle, exposing more of the conductive stripes.

FIGS. 12a and 12b shows the benefits of increased sensor resolution. FIG. 12a shows a two-stripe trilaminate needle electrode 80 penetrating the wall 81 of a vein 82. Electrical conductive stripes 83 and 84 are inserted into the wall up to the insulating layer 85. In FIG. 12b the only difference is that the insulating layer 87 is located further up the needle 80 shaft, thereby exposing more of stripes 88 and 89. In FIG. 12a the conductance of the liquid in the vein is being measured. The smaller exposed area facilitates localized measurements of conductance in the vein. Whereas in FIG. 12b, the conductance of the liquid in the vein and that of surrounding tissue is measured. The electrode needle in FIG. 12a is more likely to detect the transition to a vein from the surrounding tissue before the needle in FIG. 12b. The transition in resolution from having the whole end of the needle exposed to just the very tip as in FIG. 12a could be an order of magnitude higher.

The distance between the tips of each stripe or electrode placed on the needle shaft is also important. If the electrodes are too far apart then some subtle changes in conductance may not be easily identifiable. The closer the spacing between the electrode tips the easier it is to detect a change in resistance level. Conversely, if the spacing is too close, some object may become lodged between the electrodes causing inaccurate readings.

A prototype that was constructed used a silver suspension in enamel as a conductive layer. With the super high impedance front end circuitry of today, stainless steel works as well as precious metals. The sensor layer stripe can be evaporated onto the needle, baked as enamel, vacuum deposited or applied lithographically. The stripes are positioned along the shaft of the needle from the very tip of the penetrating end of the needle to the distal end. The connections from the stripes on the needle to the system are made in accordance with the prior art.

There has been described here a novel invention. It is evident that those skilled in the art may now make numerous uses and modifications of and departures from the inventive concepts. Consequently the invention is to be construed as embracing each and every feature and novel combination of features present or possessed by the venipuncture method and system disclosed and limited solely by the spirit and scope of the appended claims.

What is claimed is:

1. Method of determining when a hypodermic needle penetrates into tissue, vein, or lumen; said method comprising:

providing a hypodermic needle having two electrically conducting portions defined thereon, spaced apart from each other, and near a point on the hypodermic needle, and electrically insulated from each other; said conducting portions being adapted to be connected to an electrical source to enable electrical current to flow through said conducting portions;

determining the change in the electrical current between said conducting portions when said hypodermic needle is penetrating a body; and generating a signal indicating when said conducting portions have penetrated said body and reached a predetermined position.

2. The method according to claim 1, wherein said signal is audible.

3. The method according to claim 1, wherein said signal is visual.

4. The method according to claim 1, wherein said signal is both audible and visual.

* * * * *